(12) United States Patent
Chen et al.

(10) Patent No.: US 8,444,705 B2
(45) Date of Patent: May 21, 2013

(54) KNEE JOINT PROSTHESIS

(76) Inventors: Chien-Wen Chen, New Taipei (TW);
Chien-Cheng Chen, New Taipei (TW)

( * ) Notice: Subject to any disclaimer, the term of this patent is extended or adjusted under 35 U.S.C. 154(b) by 0 days.

(21) Appl. No.: 13/308,014

(22) Filed: Nov. 30, 2011

(65) Prior Publication Data
US 2012/0330440 A1    Dec. 27, 2012

(51) Int. Cl.
*A61F 2/48*    (2006.01)

(52) U.S. Cl.
USPC ............................................. 623/44

(58) Field of Classification Search
USPC ..................................... 623/41–46
See application file for complete search history.

(56) References Cited

U.S. PATENT DOCUMENTS 5,728,173 A * 3/1998 Chen ................................. 623/44
6,706,074 B1 * 3/2004 Chen ................................. 623/44

* cited by examiner

*Primary Examiner* — Bruce E Snow
(74) *Attorney, Agent, or Firm* — Banner & Witcoff, Ltd.

(57) ABSTRACT

A knee joint prosthesis is adapted for interconnecting a prosthetic lower leg and a prosthetic thigh. The knee joint prosthesis includes a knee seat disposed under and connected to the prosthetic thigh, a connecting seat disposed above and connected to the prosthetic lower leg, a link assembly, and an adjusting unit. The link assembly includes a plurality of links each connected pivotally to the knee seat and the connecting seat in such a manner to allow the knee joint prosthesis to change between an elevated position and a flexed position. The adjusting unit is disposed in the knee seat, and is operable to cooperate with the link assembly to adjust difficulty level of changing the knee joint prosthesis between the elevated and flexed positions.

6 Claims, 6 Drawing Sheets

KNEE JOINT PROSTHESIS

BACKGROUND OF THE INVENTION

1. Field of the Invention

This invention relates to a prosthetic device, and more particularly to a knee joint prosthesis.

2. Description of the Related Art

To meet the safety requirements, a conventional knee joint prosthesis is designed to have a strong support when it is flexed. However, such a design increases the difficulty level of changing the knee joint prosthesis between an elevated position and a flexed position. Hence, it is desirable that a knee joint prosthesis has the advantages of enhanced safety and low difficulty level of changing between the elevated position and the flexed position.

SUMMARY OF THE INVENTION

The object of this invention is to provide a safety knee joint prosthesis that can be changed easily between an elevated position and a flexed position.

According to this invention, a knee joint prosthesis is adapted for interconnecting a prosthetic lower leg and a prosthetic thigh. The knee joint prosthesis includes a knee seat adapted to be disposed under and connected to the prosthetic thigh, a connecting seat adapted to be disposed above and connected to the prosthetic lower leg, a link assembly, and an adjusting unit. The link assembly includes a plurality of links each connected pivotally to the knee seat and the connecting seat in such a manner to permit the knee joint prosthesis to change between an elevated position and a flexed position. The adjusting unit is disposed in the knee seat, and is operable to cooperate with the link assembly to adjust difficulty level of changing the knee joint prosthesis between the elevated and flexed positions.

BRIEF DESCRIPTION OF THE DRAWINGS

These and other features and advantages of this invention will become apparent in the following detailed description of a preferred embodiment of this invention, with reference to the accompanying drawings, in which.

DETAILED DESCRIPTION OF THE PREFERRED EMBODIMENT

Figure 1:
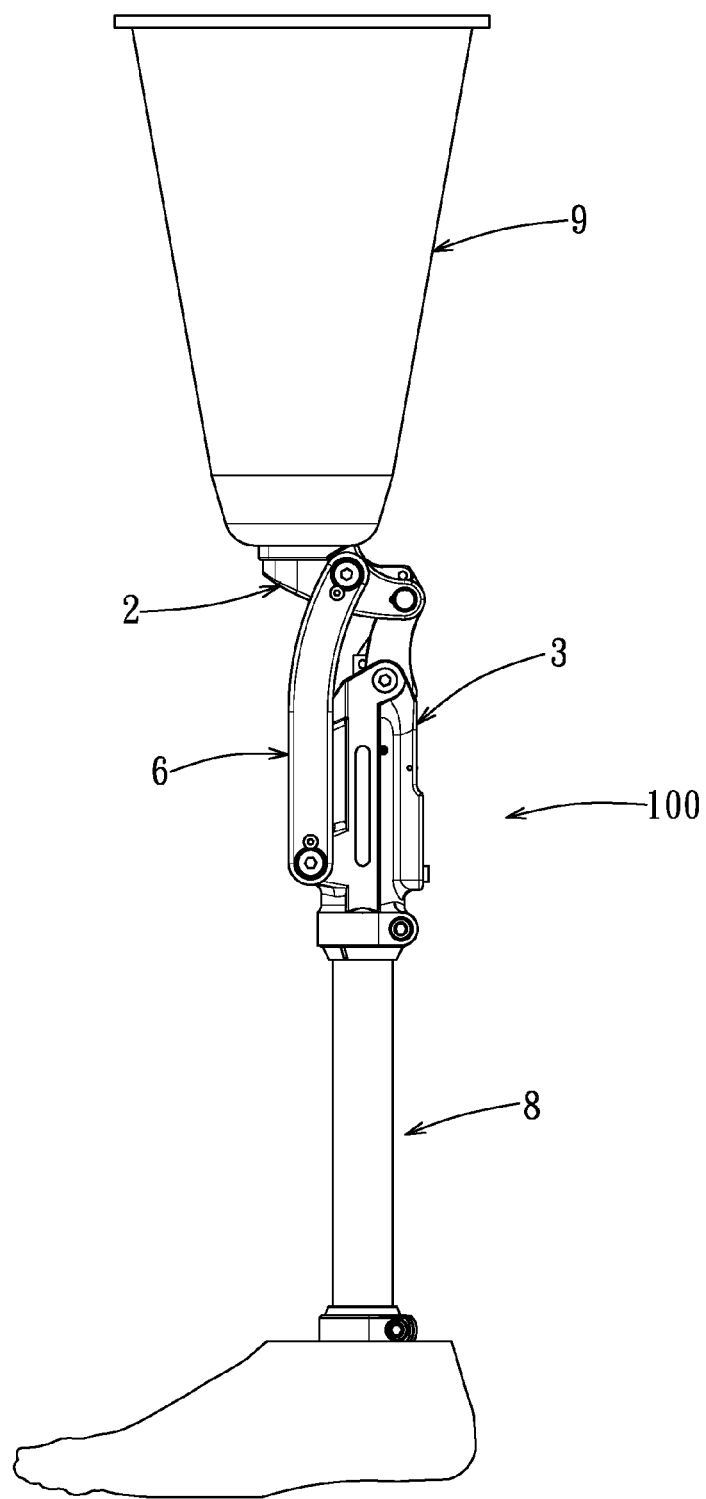
FIG. 1 is a side view of a leg prosthesis including the preferred embodiment of a knee joint prosthesis according to this invention, illustrating that the knee joint prosthesis is at an elevated position.
Figure 2:
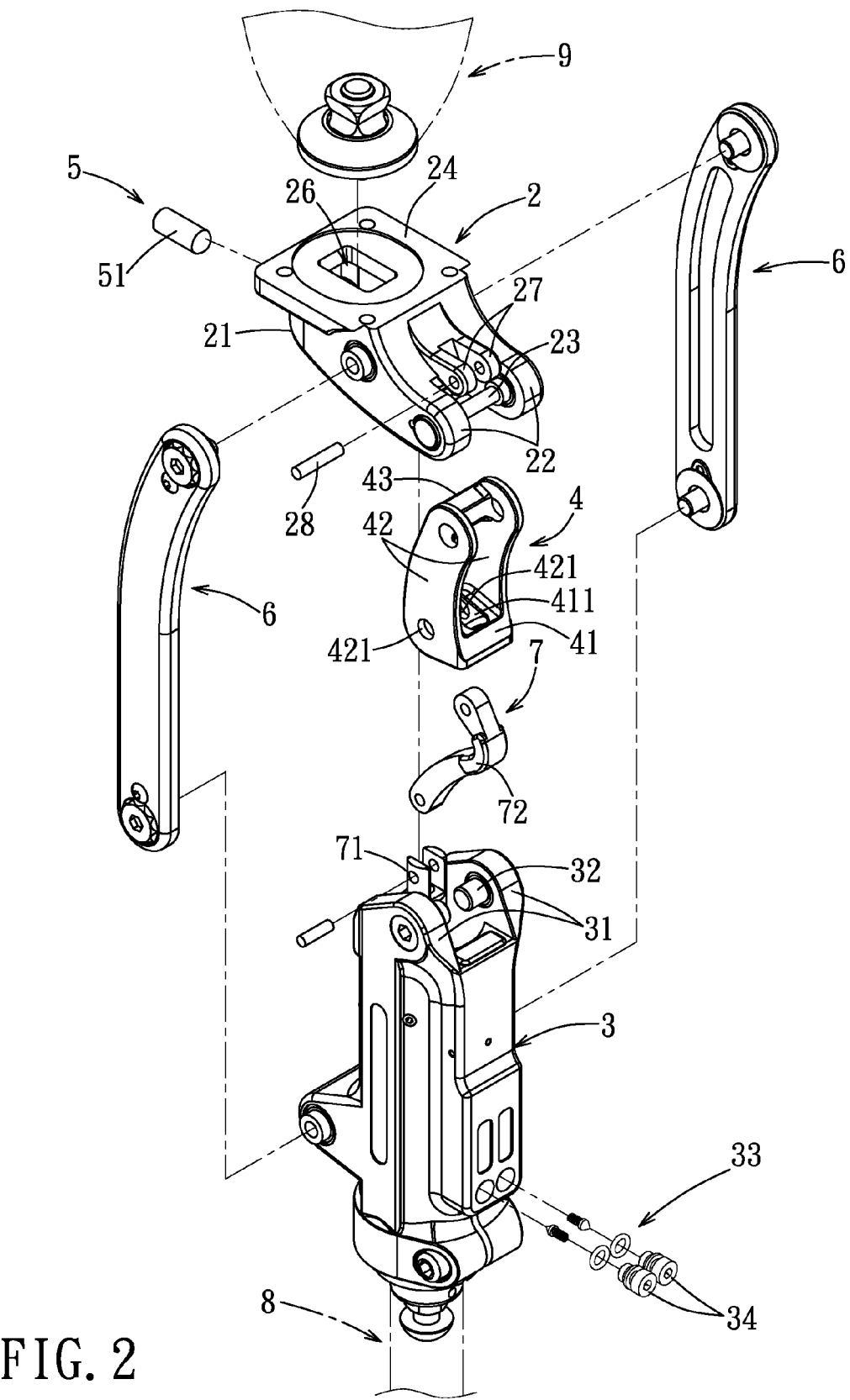
FIG. 2 is a partly exploded perspective view of the preferred embodiment.

Referring to FIGS. 1 and 2, the preferred embodiment of a knee joint prosthesis 100 according to this invention forms a portion of a leg prosthesis, and is used to interconnect a prosthetic thigh 8 and a prosthetic lower leg 9. The knee joint prosthesis 100 includes a knee seat 2 disposed below and connected to the prosthetic thigh 9, a connecting seat 3 disposed above and connected to the prosthetic lower leg 8, a link assembly consisting of a rear link 4 and two front links 6, and an adjusting unit 5.

Figure 4:
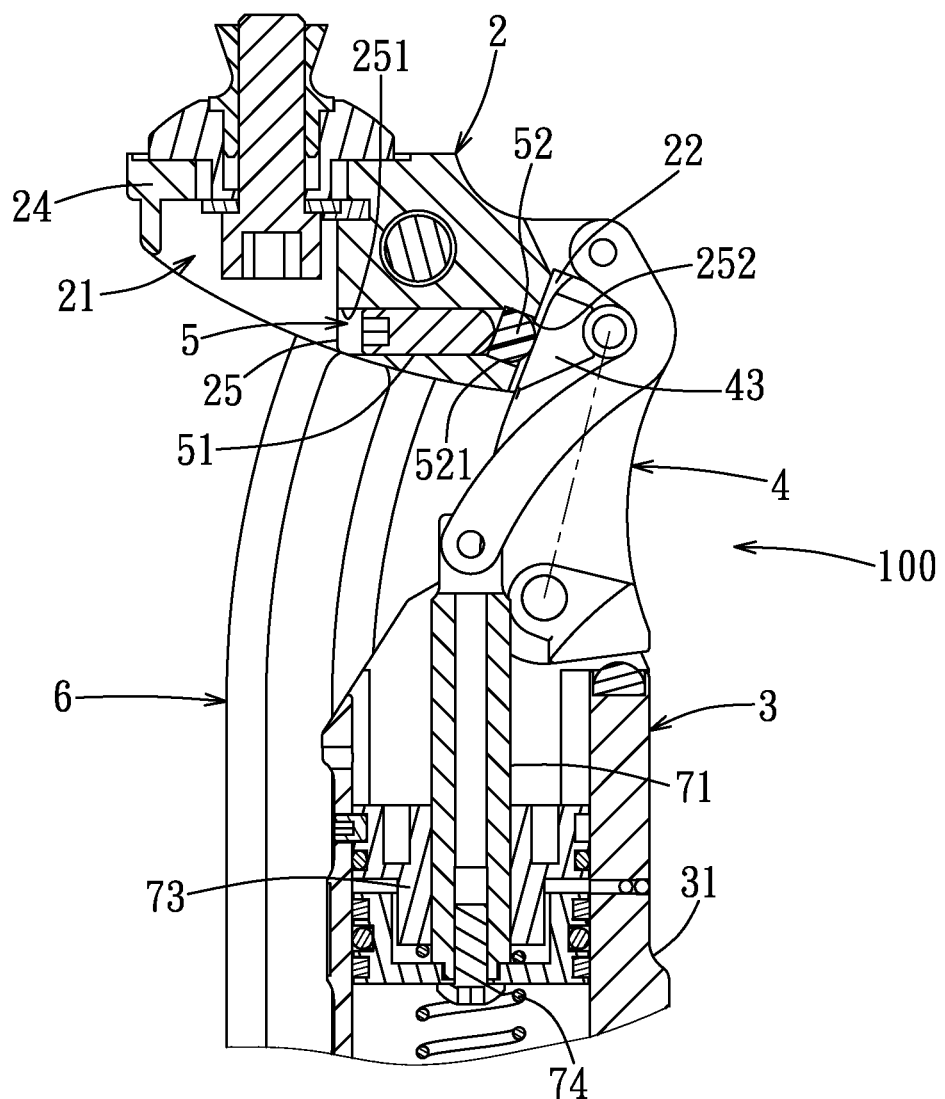
FIG. 4 is a schematic sectional view of the preferred embodiment, illustrating an adjusting unit and a damping unit.

With further reference to FIG. 4, the knee seat 2 includes a seat body 21 connected to the prosthetic thigh 9, two parallel arms 22 extending rearwardly and downwardly from the seat body 21 and spaced apart from each other in a left-to-right direction, and a pivot pin 23 extending through lower end portions of the arms 22. The seat body 21 has a top wall 24, and a receiving hole 25 formed through the seat body 21. The top wall 24 has a slide slot 26 formed therethrough and extending in a front-to-rear direction. The knee seat 2 further includes an upright lock bolt 29 extending through the slide slot 26, and is connected fixedly to the prosthetic thigh 9. When loosened from the top wall 24, the lock bolt 29 is movable along the slide slot 26, so as to adjust the position of the gravity center of the prosthetic thigh 8 relative to the knee seat 2. After the position adjustment is completed, the lock bolt 29 is locked again to the top wall 24. The receiving hole 25 has a threaded front end portion 251 and a non-threaded rear end portion 252 connected to the threaded front end portion 251. The adjusting unit 5 is received within the receiving hole 25. The knee seat 2 further includes two parallel lugs 27 extending rearwardly from the seat body 21 and disposed between the arms 22.

The front links 6 have upper ends connected respectively and pivotally to upper end portions of the arms 22 of the knee seat 2, and lower ends connected pivotally to the connecting seat 3.

Figure 3:
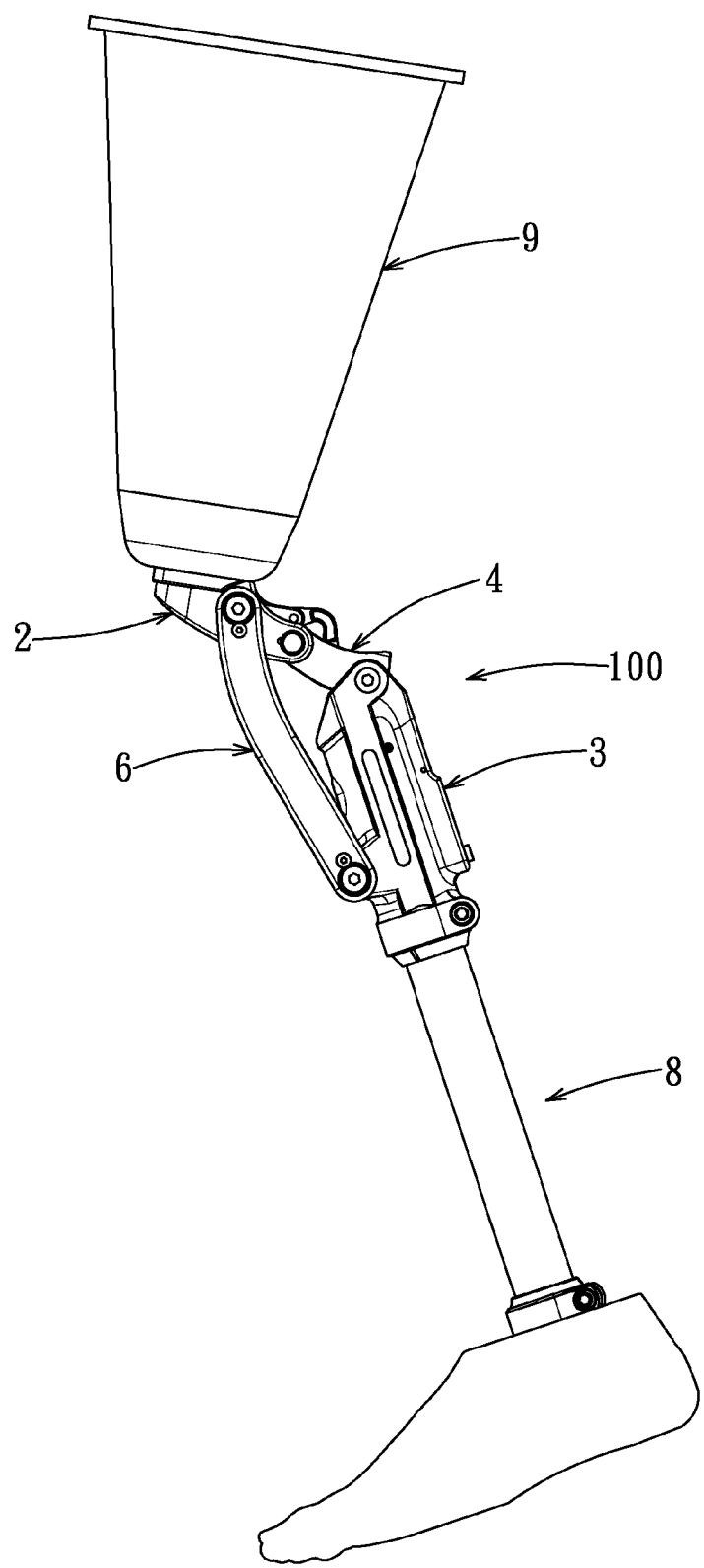
FIG. 3 is a view similar to FIG. 1 but illustrating that the knee joint prosthesis is at a flexed position.

The rear link 4 has a connecting wall 41, two side walls 42 extending respectively from two opposite sides of the connecting wall 41 and disposed between the arms 22, and a rear engaging block 43 disposed fixedly between the side walls 42 for contact with the adjusting unit 5. The side walls 42 have upper ends disposed between the arms 22 and sleeved rotatably on the pivot pin 23. The rear link 4 further has a central opening 411 formed through the connecting wall 41, and two pivot holes 421 formed respectively through lower end portions of the side walls 42. In this embodiment, the upper end of the rear link 4 is disposed behind and below the upper ends of the front links 6, and the lower end of the rear link 4 is disposed behind and above the lower ends of the front links 6. As such, the knee joint prosthesis 100 can be changed between an elevated position shown in FIG. 1 and a flexed position shown in FIG. 3.

Figure 5:
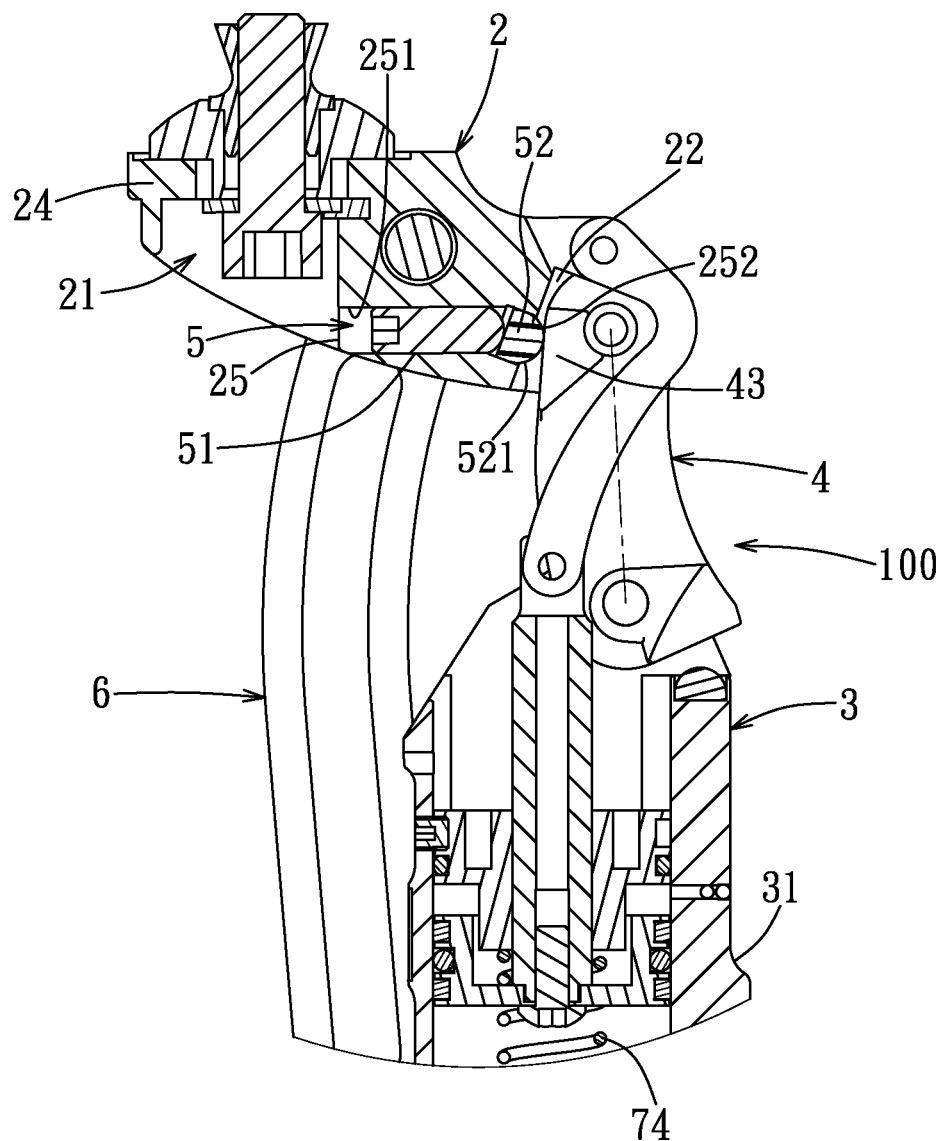
FIG. 5 is a schematic sectional view of the preferred embodiment, illustrating operation of the damping unit.
Figure 6:
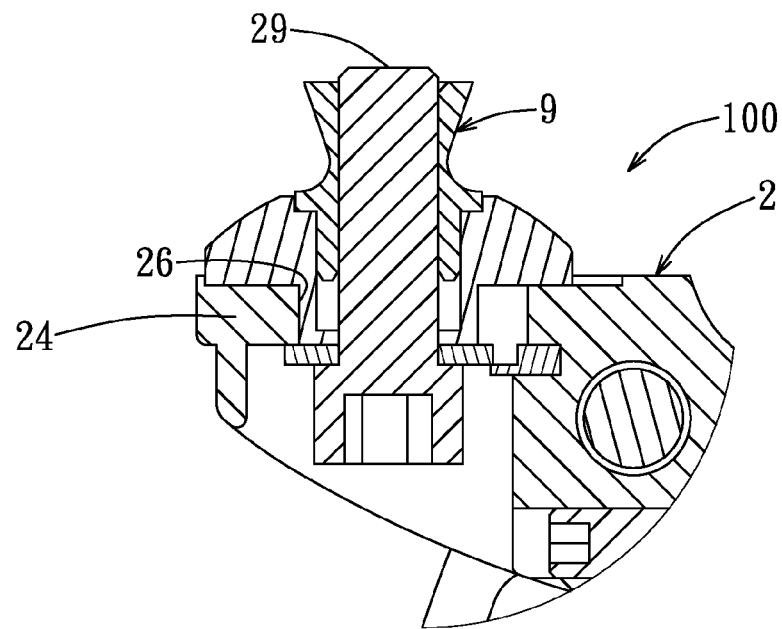
FIGS. 6 and 7 are schematic views of the preferred embodiment, illustrating how the gravity center position of a prosthetic thigh relative to a knee seat is adjusted.
Figure 7:
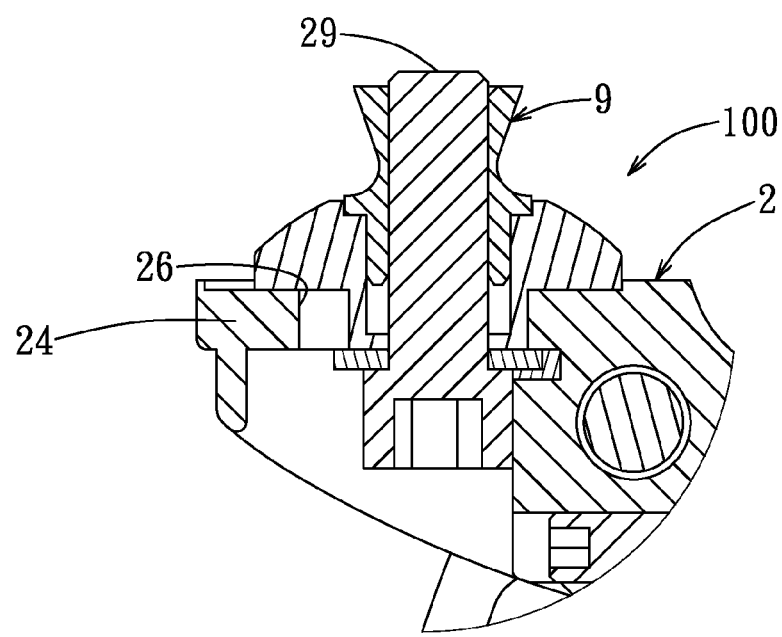

With particular reference to FIGS. 4 and 5, the adjusting unit 5 includes an adjustment bolt 51 engaging the threaded front end portion 251 of the receiving hole 25, and an elastic engaging block 52 received within the non-threaded rear end portion 252 of the receiving hole 25 and having a semi-spherical engaging surface 521 for contact with the rear engaging block 43 of the rear link 4.

The knee joint prosthesis 100 further includes a damping unit 7. The damping unit 7 includes a movable rod 71 disposed movably within the connecting seat 3, a generally V-shaped connecting rod 72 having upper end and lower ends connected respectively and pivotally to the knee seat 2 and the connecting seat 3 in such a manner that a pivot pin (see FIG. 2) extends through the upper end of the connecting rod 72 and the lugs 27, a spring-engaging member 73 sleeved fixedly on the movable rod 71, and a resilient member 74 configured as a coiled compression spring and disposed between and abutting against the spring-engaging member 73 and a bottom wall (not shown) of the connecting seat 3 for biasing the movable rod 71 to move upwardly relative to the connecting seat 3. The connecting rod 72 extends through the opening 411 in the connecting wall 41 of the rear link 4. As such, the rear engaging block 43 is biased by the resilient member 74 toward the front engaging block 52 to thereby clamp the front engaging block 52 between the adjustment bolt 51 and the rear engaging block 43. Hence, the adjustment bolt 51 can be operated to change the position of the front engaging block 52 relative to the receiving hole 25 and, thus, the moving path of the connecting rod 72 to thereby adjust the difficulty level of changing the knee joint prosthesis 100 between the elevated position and the flexed position. In this embodiment, the connecting seat 3 includes two upright side wall portions 31 disposed at an upper end thereof, and two pivot bolts 32. The side walls 42 of the rear link 4 are disposed between the side wall portions 31 of the connecting seat 3. The pivot bolts 32 are threaded respectively through the side wall portions 31, and extend respectively through the pivot holes 421 in the side walls 42 of the rear link 4, so as to connect the lower end of the rear link 4 pivotally to the upper end of the connecting seat 3.

Preferably, a hydraulic or pneumatic damping-action adjusting unit 33 is provided for adjusting the damping action of the damping unit 7, and includes two adjustment bolts 34 threaded into the connecting seat 3 and operable to adjust the flow rate of a fluid flowing in the connecting seat 3.

In view of the above, due to the presence of the adjusting unit 5, the difficulty level of changing the knee joint prosthesis 100 between the elevated position and the flexed position can be adjusted. Thus, the object of this invention is achieved.

With this invention thus explained, it is apparent that numerous modifications and variations can be made without departing from the scope and spirit of this invention. It is therefore intended that this invention be limited only as indicated by the appended claims.

We claim:

1. A knee joint prosthesis adapted for interconnecting a prosthetic lower leg and a prosthetic thigh, said knee joint prosthesis comprising:
    a knee seat adapted to be disposed under and connected to the prosthetic thigh;
    a connecting seat adapted to be disposed above and connected to the prosthetic lower leg;
    a link assembly including a plurality of links each connected pivotally to said knee seat and said connecting seat in such a manner to allow said knee joint prosthesis to change between an elevated position and a flexed position; and
    an adjusting unit disposed in said knee seat and operable to cooperate with said link assembly to adjust difficulty level of changing said knee joint prosthesis between the elevated and flexed positions;
    wherein:
    said knee seat includes
        a seat body adapted to be connected to the prosthetic thigh, and
        two parallel arms extending rearwardly and downwardly from said seat body and spaced apart from each other in a left-to-right direction; and
    said links of said link assembly include
        two front links each having upper ends connected respectively and pivotally to upper end portions of said arms of said knee seat, and lower ends connected pivotally to said connecting seat, and
        a rear link having a connecting wall and two side walls extending respectively from two opposite sides of said connecting wall and disposed between said arms, said side walls having upper ends disposed between said arms and connected respectively and pivotally lower end portions of said arms.

2. The knee joint prosthesis as claimed in claim 1, wherein said links of said link assembly include:
    said two front links each having upper and lower ends connected respectively and pivotally to said knee seat and said connecting seat, and
    said rear link having an upper end connected pivotally to said knee seat and disposed behind and below said upper ends of said front links, and a lower end connected pivotally to said connecting seat and disposed behind and above said lower ends of said front links.

3. The knee joint prosthesis as claimed in claim 1, further comprising a damping unit, said damping unit including a movable rod disposed movably within said connecting seat, a connecting rod having upper and lower ends connected respectively and pivotally to said knee seat and said connecting seat, and a resilient member for biasing said movable rod to move upwardly relative to said connecting seat.

4. The knee joint prosthesis as claimed in claim 1, wherein:
    said rear link further has a central opening formed through said connecting wall, and two pivot holes formed respectively through lower end portions of said side walls;
    said connecting seat includes two upright side wall portions at an upper end thereof, and two pivot bolts each extending through a respective one of said upright side wall portions and a respective one of said side walls of said rear link, said connecting wall of said rear link being disposed between said side wall portions of said connecting seat; and
    said knee joint prosthesis further comprises a damping unit, said damping unit including a movable rod disposed movably within said connecting seat, a connecting rod having upper and lower ends connected respectively and pivotally to said knee seat and said connecting seat, and a resilient member for biasing said movable rod to move upwardly relative to said connecting seat, said connecting rod extending through said opening in said connecting wall of said rear link.

5. The knee joint prosthesis as claimed in claim 4, wherein:
    said rear link further has a rear engaging block disposed fixedly between said side walls;
    said seat body of said knee seat is formed with a receiving hole therethrough, said receiving hole having a threaded front end portion and a non-threaded rear end portion connected to the threaded front end portion; and
    said adjusting unit includes an adjustment bolt engaging said threaded front end portion of said receiving hole in said seat body of said knee seat, and an elastic front engaging block disposed within said non-threaded rear end portion of said receiving hole, in such a manner that said front engaging block is clamped between said adjustment bolt and said rear engaging block by virtue of the biasing action of said resilient member, said adjustment bolt being operable to adjust the difficulty level of changing said knee joint prosthesis between the elevated and flexed positions.

6. The knee joint prosthesis as claimed in claim 1, wherein said seat body of said knee seat has a top wall, said top wall having a slide slot formed therethrough and extending in a front-to-rear direction, said knee seat further including an upright lock bolt extending through said slide slot and adapted to be connected fixedly to the prosthetic thigh, said lock bolt being operable to move along said slide slot so as to adjust the position of the gravity center of the prosthetic thigh relative to said knee seat.

* * * * *